(12) United States Patent
Lebosse et al.

(10) Patent No.: US 8,303,478 B2
(45) Date of Patent: Nov. 6, 2012

(54) ROBOTIZED INSTALLATION FOR THE POSITIONING AND MOVEMENT OF A COMPONENT OR INSTRUMENT AND TREATMENT DEVICE THAT COMPRISES SUCH AN INSTALLATION

(75) Inventors: Cyrille Lebosse, Luxembourg (LU); Pierre Renaud, Schiltigheim (FR); Bernard Bayle, Strasbourg (FR); Michel De Mathelin, Strasbourg (FR); Olivier Piccin, Mittelhausen (FR); Edouard Laroche, Strasbourg (FR)

(73) Assignees: Universite de Strasbourg, Strasbourg (FR); Centre National de la Recherche Scientifique, Paris (FR); Institut National des Sciences Appliquees, Strasbourg (FR)

( * ) Notice: Subject to any disclaimer, the term of this patent is extended or adjusted under 35 U.S.C. 154(b) by 860 days.

(21) Appl. No.: 12/306,806

(22) PCT Filed: Jun. 26, 2007

(86) PCT No.: PCT/FR2007/051518
§ 371 (c)(1),
(2), (4) Date: Dec. 29, 2008

(87) PCT Pub. No.: WO2008/001003
PCT Pub. Date: Jan. 3, 2008

(65) Prior Publication Data
US 2009/0216067 A1    Aug. 27, 2009

Related U.S. Application Data

(60) Provisional application No. 60/816,343, filed on Jun. 26, 2006.

(51) Int. Cl.
*A61N 2/02* (2006.01)

(52) U.S. Cl. .......................................................... 600/13
(58) Field of Classification Search .......... 378/167–203; 600/9–15
See application file for complete search history.

(56) References Cited

U.S. PATENT DOCUMENTS 5,749,362 A    5/1998  Funda et al.
(Continued)

FOREIGN PATENT DOCUMENTS

| DE | 199 26 977 | 1/2001 |
| DE | 102 42 542 | 4/2004 |
| WO | 03/098268 | 11/2003 |

OTHER PUBLICATIONS

International Search Report dated Apr. 28, 2008, from corresponding PCT application.

*Primary Examiner* — Charles A Marmor, II
*Assistant Examiner* — Catherine E Burk
(74) *Attorney, Agent, or Firm* — Young & Thompson

(57) ABSTRACT

Robotized installation for the guided and controlled positioning and movement of a component or an instrument for diagnostic or surgical treatment at or around the head of a patient, whereby the installation includes a robotic device that forms a serial kinematic chain and carries component or instrument at its free and position-controlled end. The robotic device has three kinematic sub-assemblies that are mutually combined in series and include, a first sub-assembly in the form of a rotary-articulation mechanism corresponding to a serial-type, spherical kinematic arrangement with three degrees of freedom, a second sub-assembly in the form of a mechanism with linear translation along an axis, and a third sub-assembly in the form of a second rotary-articulation mechanism, integral with the moving part of the second sub-assembly and also corresponding to a serial-type spherical kinematic arrangement with three degrees of freedom.

20 Claims, 14 Drawing Sheets

U.S. PATENT DOCUMENTS

Figure 1:
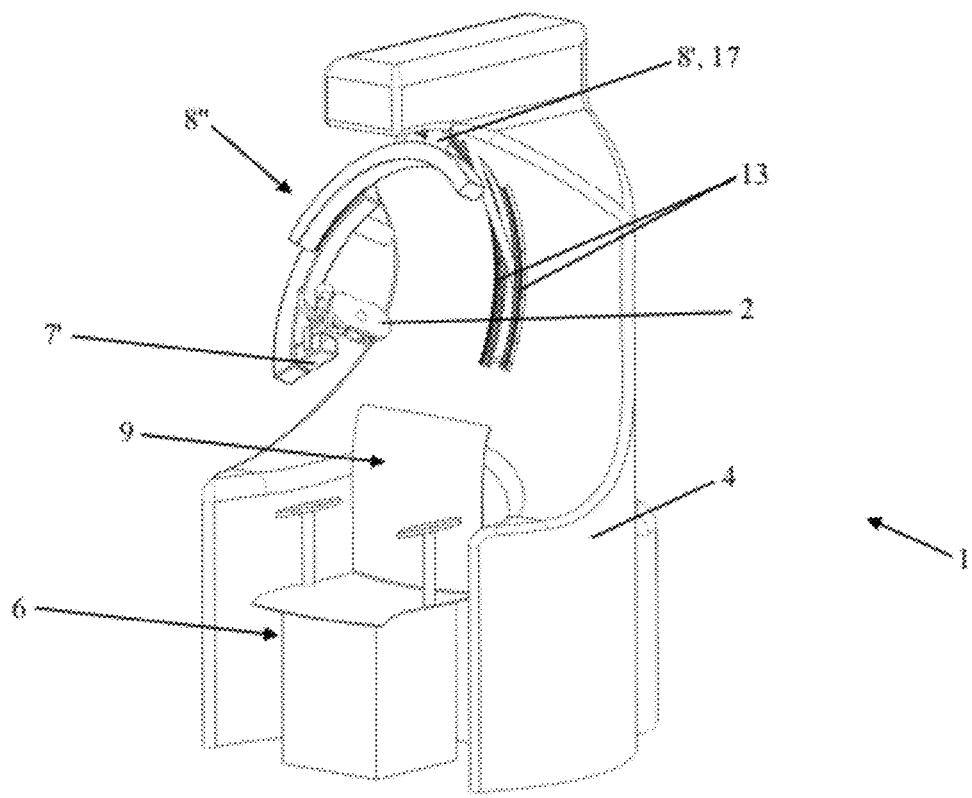
Figure 2:
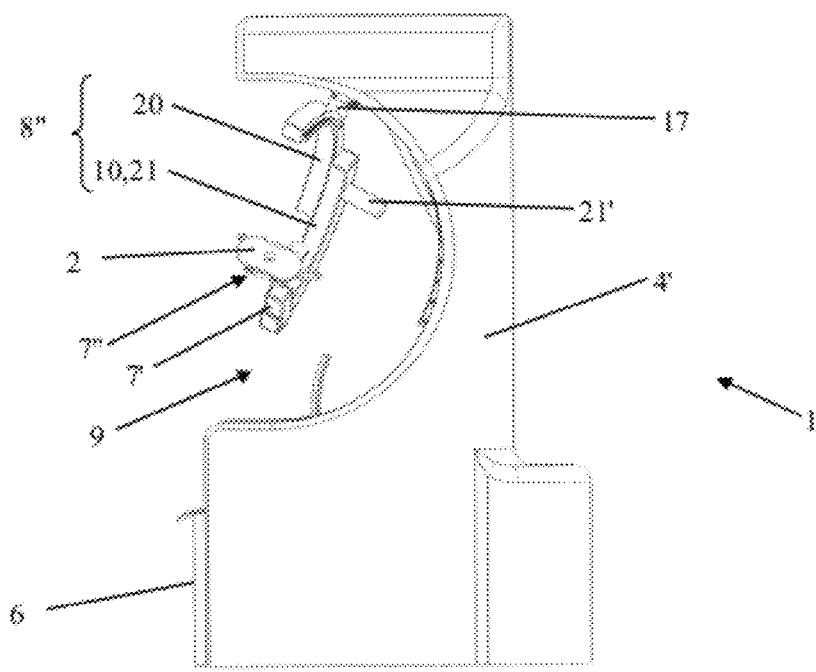
Figure 3:
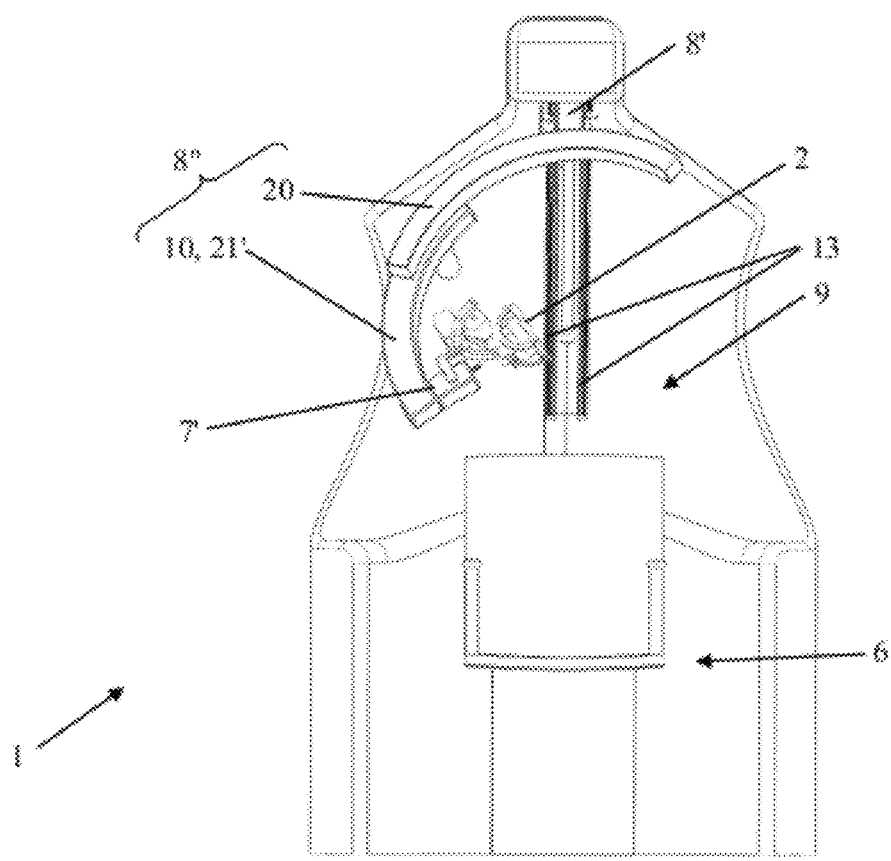
Figure 4:
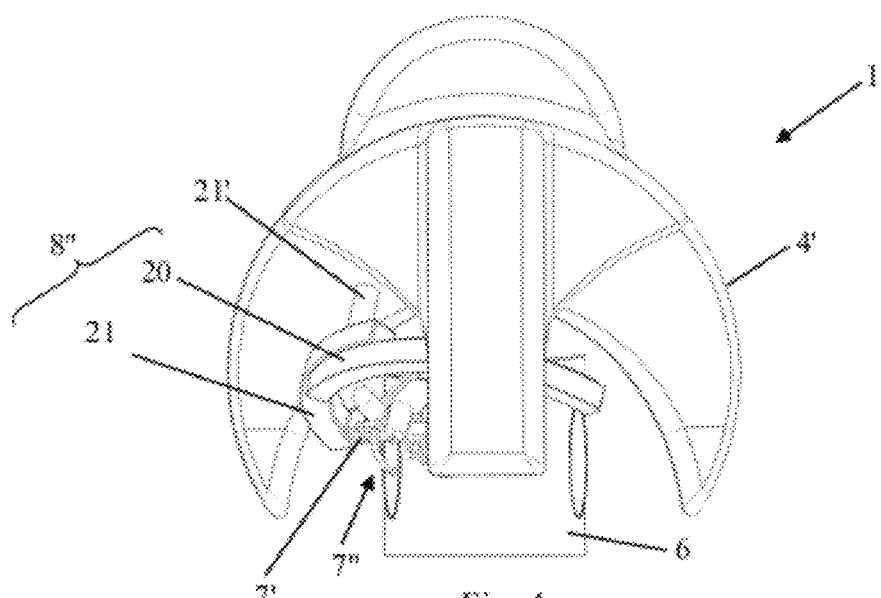

| | | | |
|---|---|---|---|
| 6,428,206 B1 * | 8/2002 | Watanabe | 378/197 |
| 6,665,554 B1 * | 12/2003 | Charles et al. | 600/427 |
| 6,819,737 B2 * | 11/2004 | Suzuki et al. | 378/15 |
| 6,830,544 B2 * | 12/2004 | Tanner | 600/9 |
| 2005/0049486 A1 * | 3/2005 | Urquhart et al. | 600/429 |
| 2005/0228209 A1 | 10/2005 | Schneider et al. | |
| 2005/0234286 A1 * | 10/2005 | Riehl et al. | 600/9 |
| 2006/0122496 A1 | 6/2006 | George et al. | |
| 2006/0161039 A1 * | 7/2006 | Juliana et al. | 600/9 |

\* cited by examiner

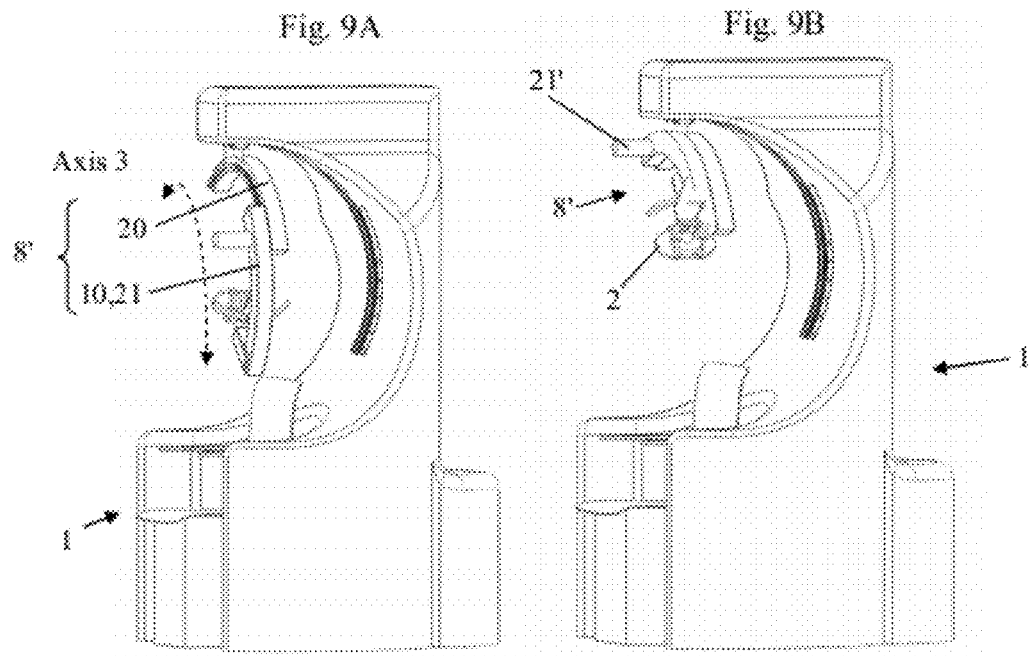
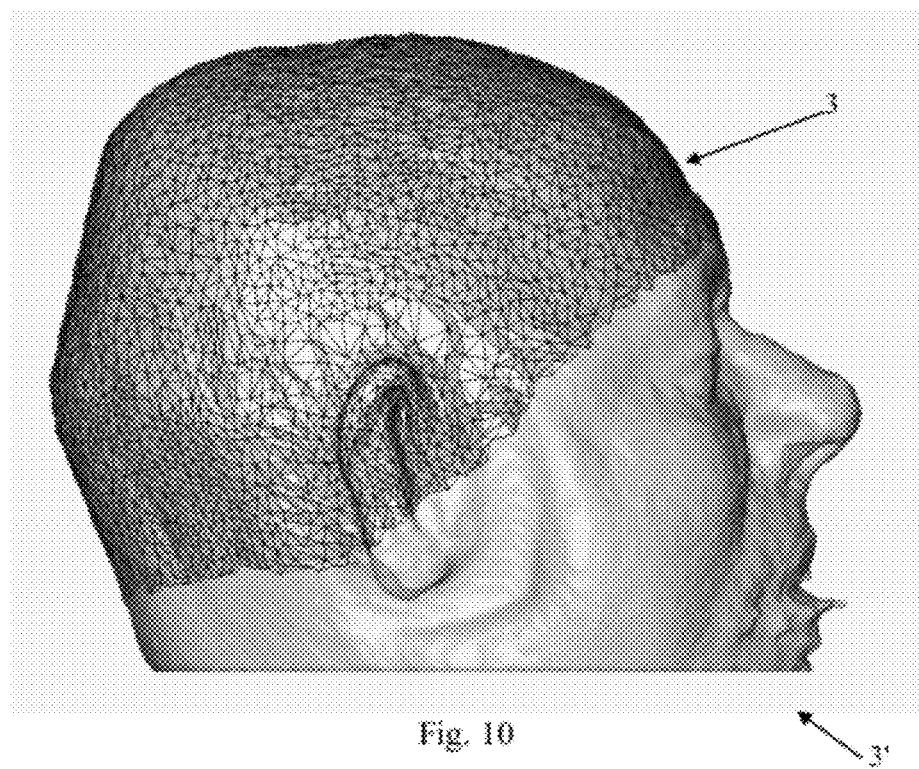
Fig. 10

ROBOTIZED INSTALLATION FOR THE POSITIONING AND MOVEMENT OF A COMPONENT OR INSTRUMENT AND TREATMENT DEVICE THAT COMPRISES SUCH AN INSTALLATION

BACKGROUND OF THE INVENTION

1. Field of the Invention

This invention relates to the field of robotic installations and devices that have a high precision and a very good safety of use, allowing their implementation in a medical context.

2. Description of the Related Art

This invention more particularly has as its object a robotized installation for the positioning and the movement of a component or instrument, a transcranial magnetic stimulation device that comprises such a robotized installation and a transcranial magnetic stimulation process that implements the above-mentioned device.

In numerous procedures for treating patients or for medical imagery, it is necessary to carry out precise and repeated positionings and movements of components or instruments if necessary over often consistent lengths of time (several tens of minutes).

These experiments are tedious and exhausting for the operator, even when they are assisted mechanically to facilitate the execution thereof.

In addition, the operator should necessarily be a specialized individual, i.e., in general a surgeon, a neurologist, a radiologist or an analogous specialist, depending on the components in question and the type of treatment or investigation to be carried out.

In addition, even an experienced operator, optionally able to exploit a visual return provided by a navigation system, cannot ensure a positioning or a movement in optimum agreement with previously calculated data nor a fortiori the identical repetition of a given procedure, requiring several similar successive applications to be effective.

Finally, according to the type of treatment or investigation to be carried out, the operator that manually handles the component or the instrument is exposed to a harmful radiation.

These different factors explain the demand of practitioners for the implementation of robotized installations.

Several problems disclosed above are posed in particular relative to the transcranial magnetic stimulation that is designed to issue electrical stimulation to the cerebral cortex.

The effectiveness of this process was demonstrated in the case of depression, and studies are currently being conducted for pathologies other than post-traumatic anxiety, obsessive-compulsive disorders, schizophrenia, and even for certain types of epileptic disorders.

However, a significant variability of the effectiveness according to the patient that is primarily due to the difficulty of the handling of the kind of stimulation system as it currently exists and that makes it almost impossible to reproduce the same procedure identically has been observed.

Actually, during the implementation of the current procedures, as soon as the target zone of the cortex has been defined by the functional use of MRI images, the probe that integrates the magnetic stimulation coil is to be moved manually on the patient's head by the neurologist in order to follow the precise path in space.

However, even when a visual follow-up is provided to the neurologist by a navigation system for the purpose of facilitating the positioning of the coil, it was noted that in practice, it was impossible to obtain a precise movement of the probe.

In addition, such a manual treatment is extremely detrimental in terms of the price of the procedure, taking into account the necessary qualification of the operator and the significant duration of each treatment sequence.

Various implementations of robotized devices for medical use, designed to position and/or to move a component or an instrument relative to a patient, are already known.

Nevertheless, these existing systems, often derived from industrial robotic devices, are not suitable for moving a tool or an instrument at the surface of a patient, do not ensure adequate precision in terms of their movements and/or exhibit an inadequate level of safety of use for a medical application.

Furthermore, by the document "Psychiatry's Shocking New Tools" of Samuel K. Moore, IEEE Spectrum, March 2006, a theoretical representation of a transcranial magnetic stimulation device that comprises an articulated structure that supports the application probe of a pulsed magnetic field is known.

This structure, automatically piloted or controlled remotely by an operator, comprises a telescopic bracket, at the end of which is suspended, by means of a rotoidal connection, an articulated sub-assembly that carries the probe.

The sub-assembly itself comprises a moving circular rail, one of whose ends is integral, by means of a rotoidal connection, with a slide rail, on which the probe is mounted in a sliding manner.

Thus, the combination of these different articulated connections provides only five degrees of freedom and thereby only points of the upper part of the cranial cap can be reached by the probe of this device according to this document.

In addition, it seems that this structure does not make it possible to carry out a scanning from front to rear on the patient's head, and it would be necessary to complete said structure by two additional degrees of mobility in translation in a horizontal plane to be able to scan the entire upper surface of the skull.

Furthermore, no mechanism for controlling the orientation of the transcranial magnetic stimulation probe, around a contact point, is provided.

Finally, it is noted that the management of the contact effort, if it is optionally provided (the IEE Spectrum document does not mention it), would be difficult to implement taking into consideration the architecture of the structure. It is also noted that it is not possible to move the probe along a single axis in case of incident, such as a power failure, without running the risk of interfering with the patient's head, and that the multiplication of the cantilevers has a negative effect on the rigidity of the structure and the precision of the movements of the probe.

SUMMARY OF THE INVENTION

This invention has as its object to eliminate at least some of the drawbacks disclosed above and to propose a robotized solution by the various experiments suggested above, relatively simple to control and meeting the required criteria of precision and safety.

For this purpose, the invention has as its object a robotized installation for the guided and controlled positioning and movement of a component or an instrument for diagnostic or surgical treatment, in particular an imagery probe or a transcranial magnetic stimulation probe or the like, at or around the head of a patient, whereby said installation essentially comprises a support structure on which are mounted the constituent elements of a robotic device that forms a serial kinematic chain and carries the above-mentioned component or instrument at its free and position-controlled end, an adjustable device for supporting and holding the patient, essentially in seated position, forming part of or being combined with said support structure, an installation that is characterized in that said robotic device consists of at least two, preferably three, kinematic sub-assemblies that are mutually combined in series and that comprise, on the one hand, a first sub-assembly in the form of a rotary-articulation mechanism, integral with the support structure by a first articulation and corresponding to a serial-type, spherical kinematic arrangement with three degrees of freedom, whereby the articulation elements are all located outside of the space that can accommodate the patient and whereby their axes of rotation are concurrent at a focal point that corresponds approximately to the hypothetical center of the patient's head in an intervention position, and, on the other hand, a second sub-assembly in the form of a mechanism with linear translation along an axis that passes through the above-mentioned focal point that is integral with the moving part of the third articulation in series of the first sub-assembly, and finally, if necessary, a third sub-assembly in the form of a second rotary-articulation mechanism, integral with the moving part of the second sub-assembly and also corresponding to a serial-type spherical kinematic arrangement with three degrees of freedom, whereby the articulation elements of this third sub-assembly have concurrent axes of rotation.

BRIEF DESCRIPTION OF THE DRAWING FIGURES

Figure 5A:
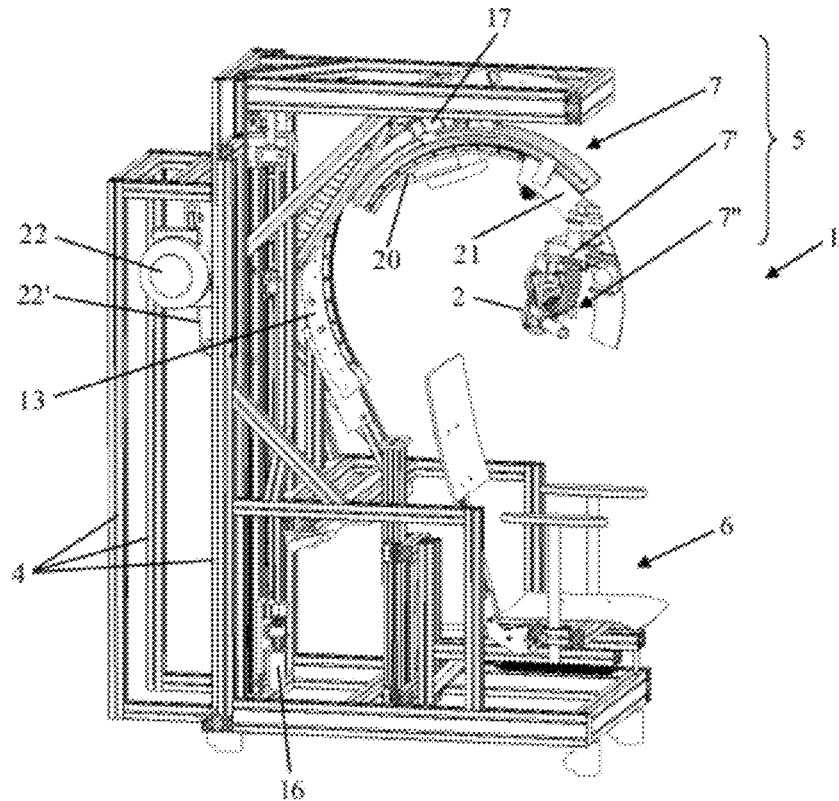
Figure 5B:
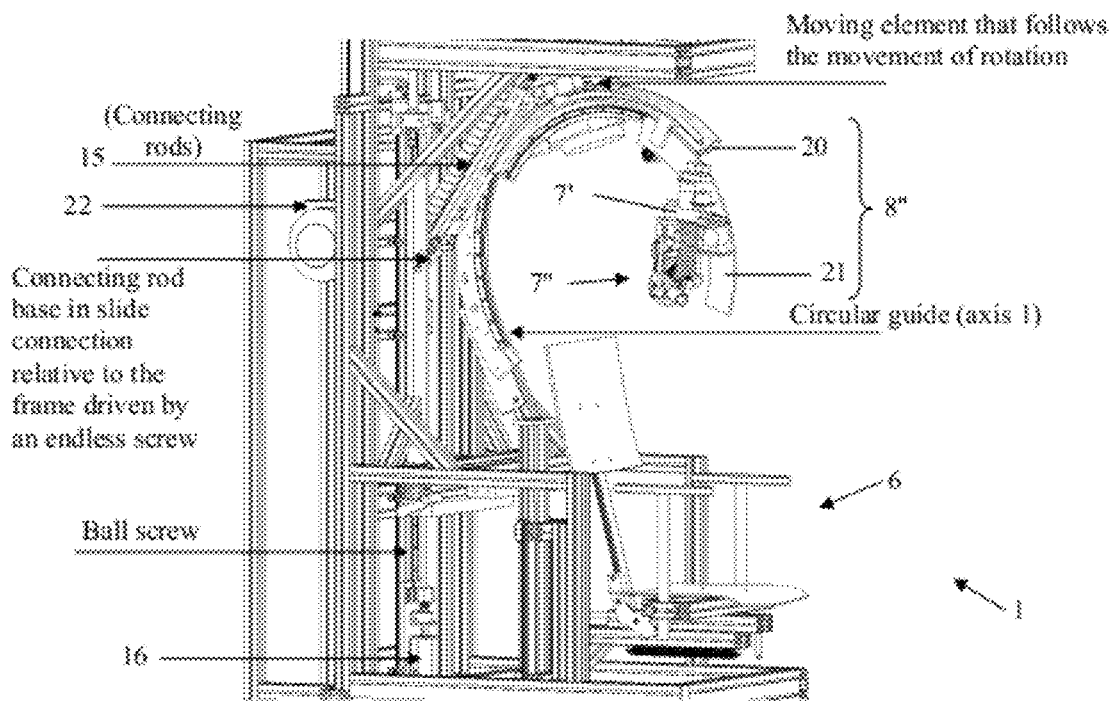
Figure 6A:
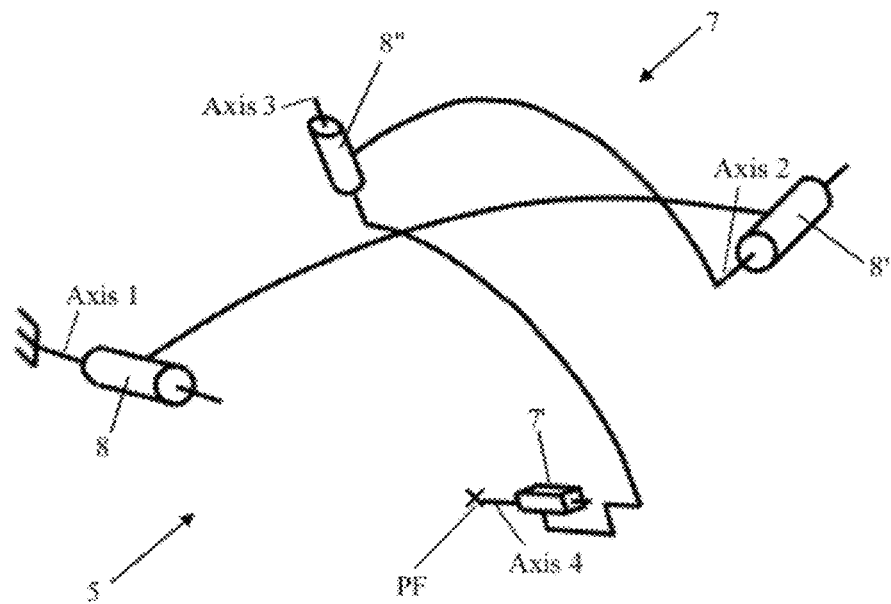
Figure 6B:
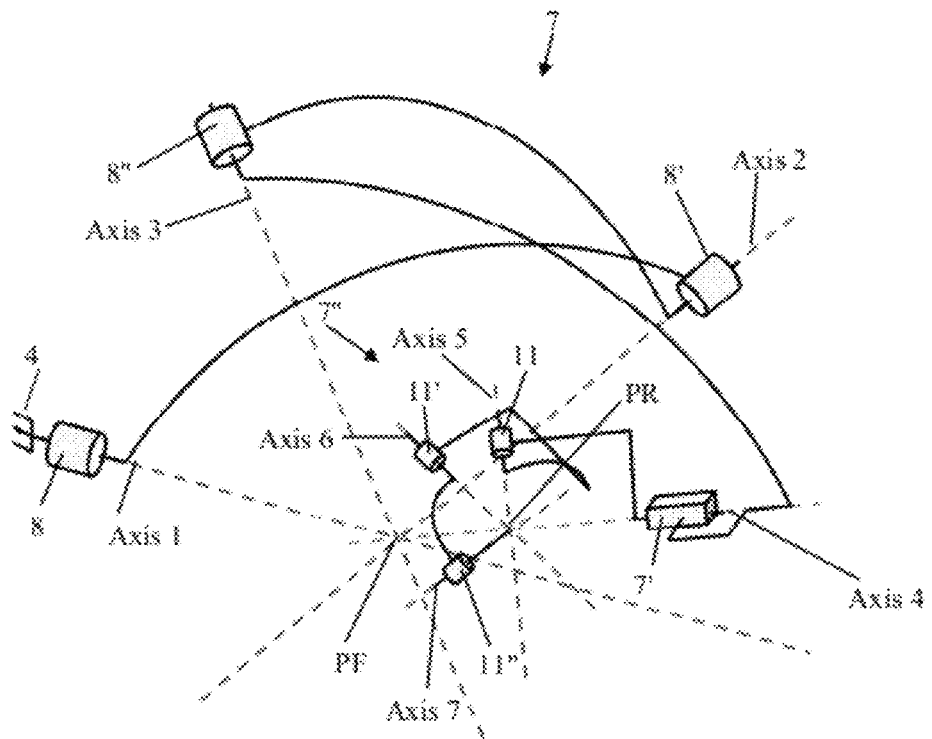
Figure 7A:
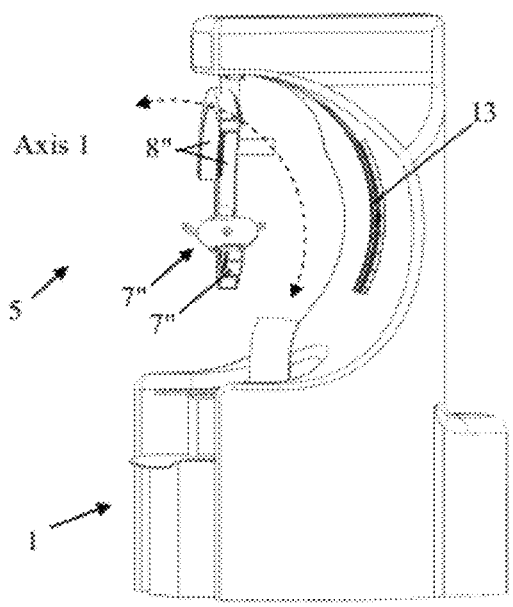
Figure 7B:
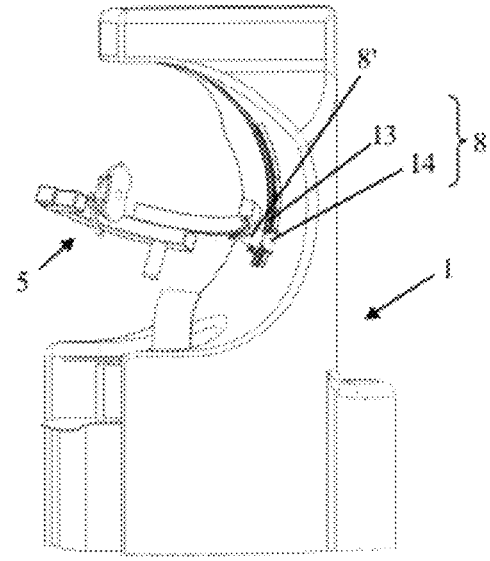
Figure 8A:
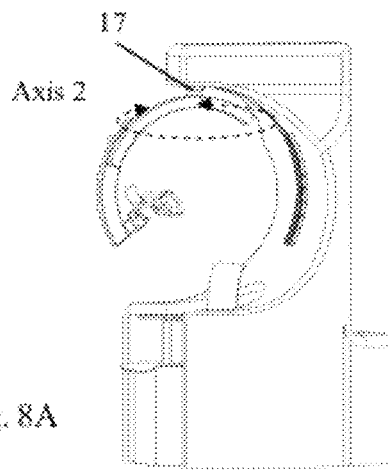
Figure 8B:
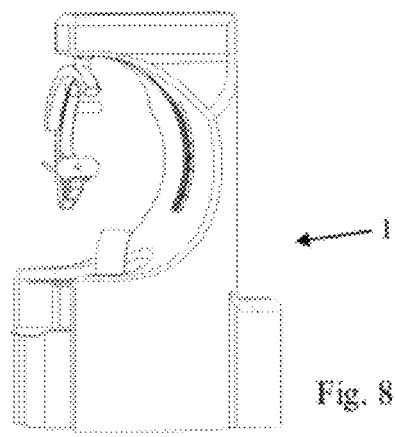
Figure 8C:
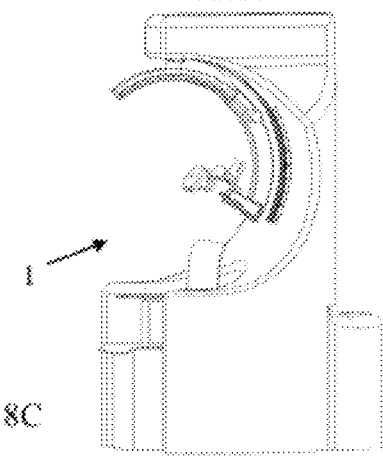
Figure 8D:
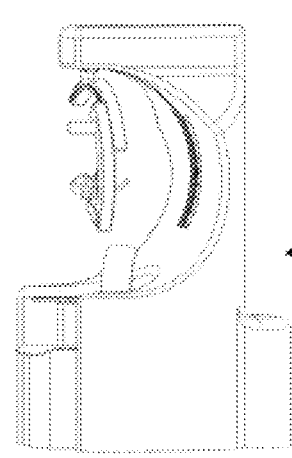
Figures 11A, 11B:
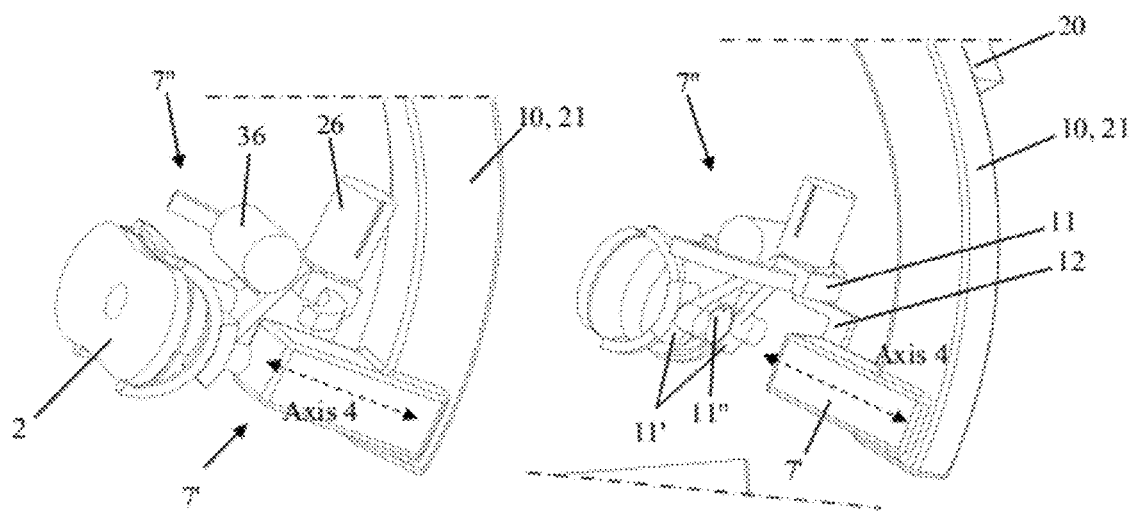
Figure 12:
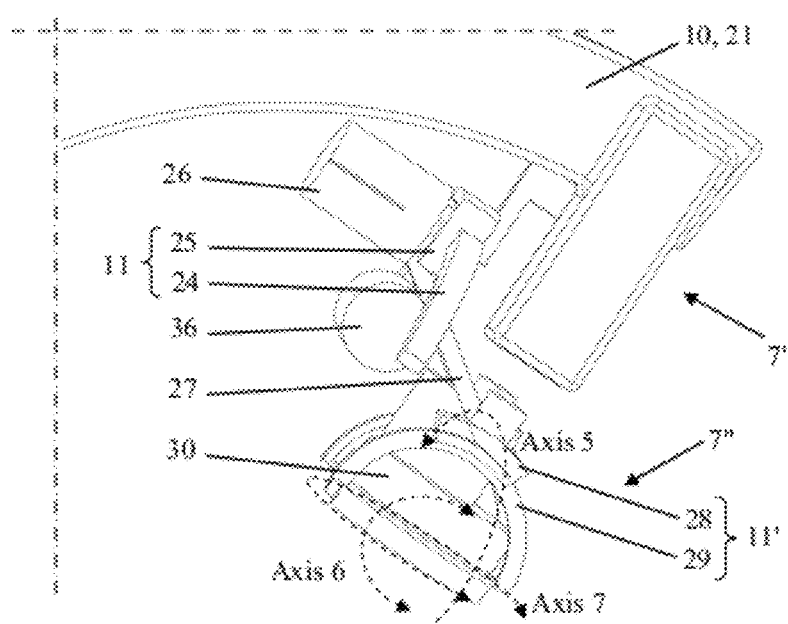
Figure 13:
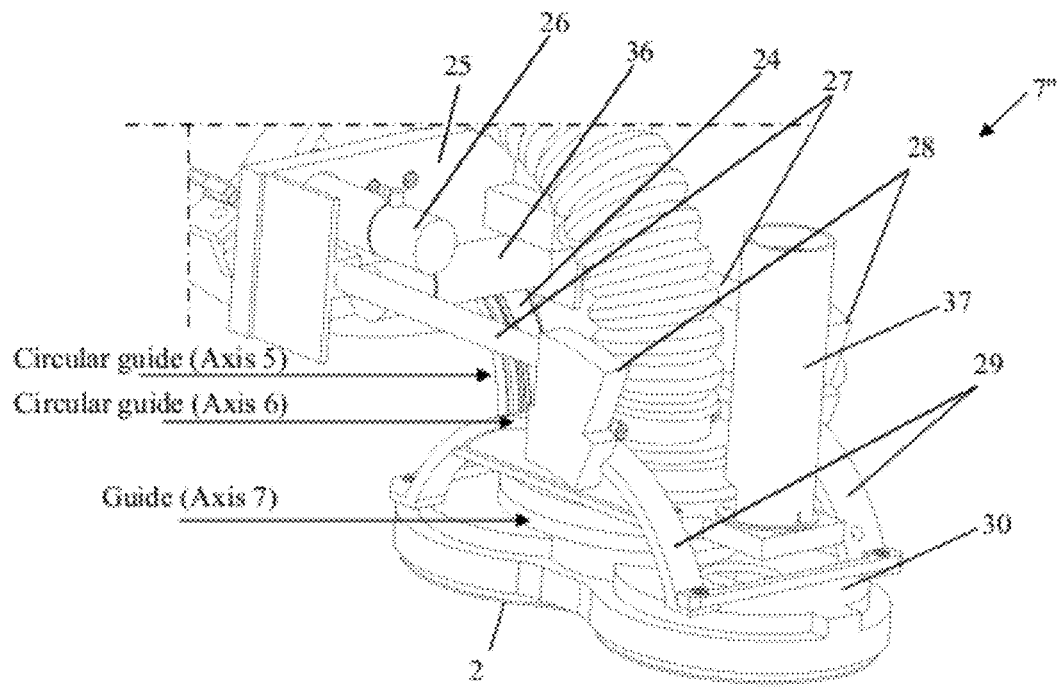
Figure 14:
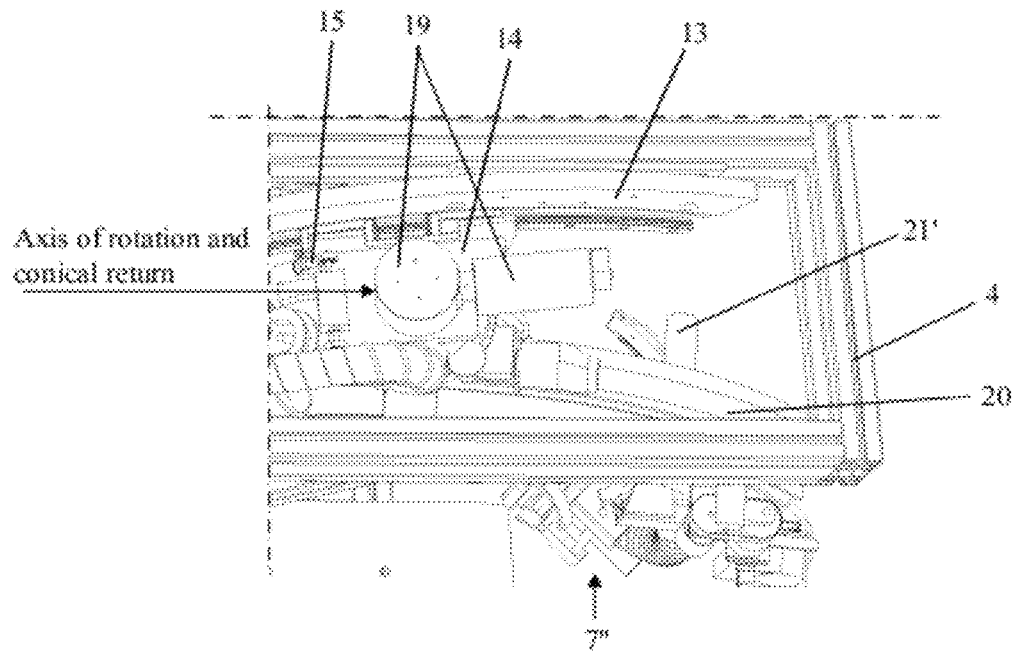
Figure 15:
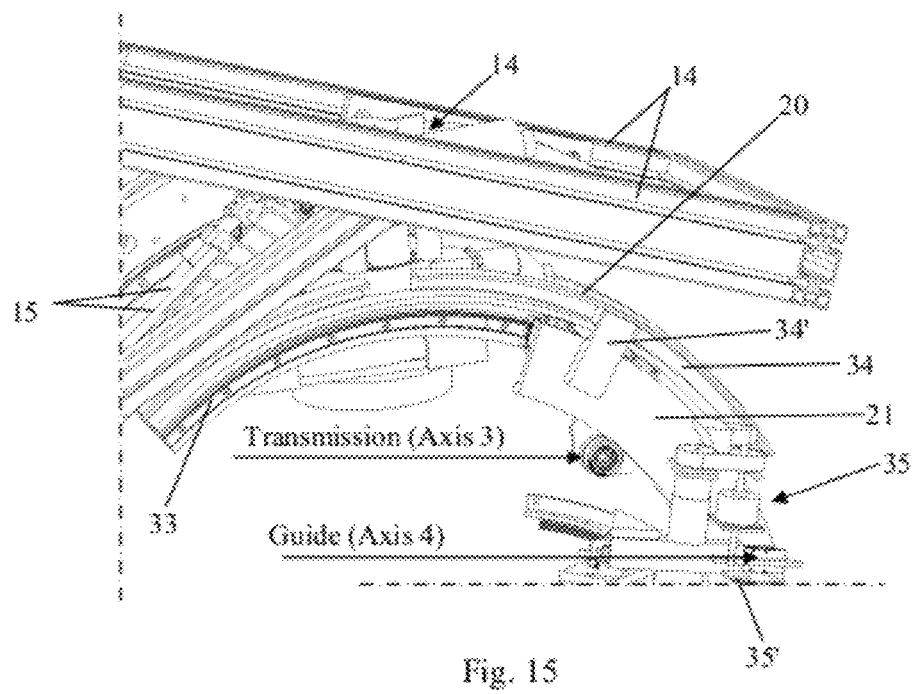
Figure 16:
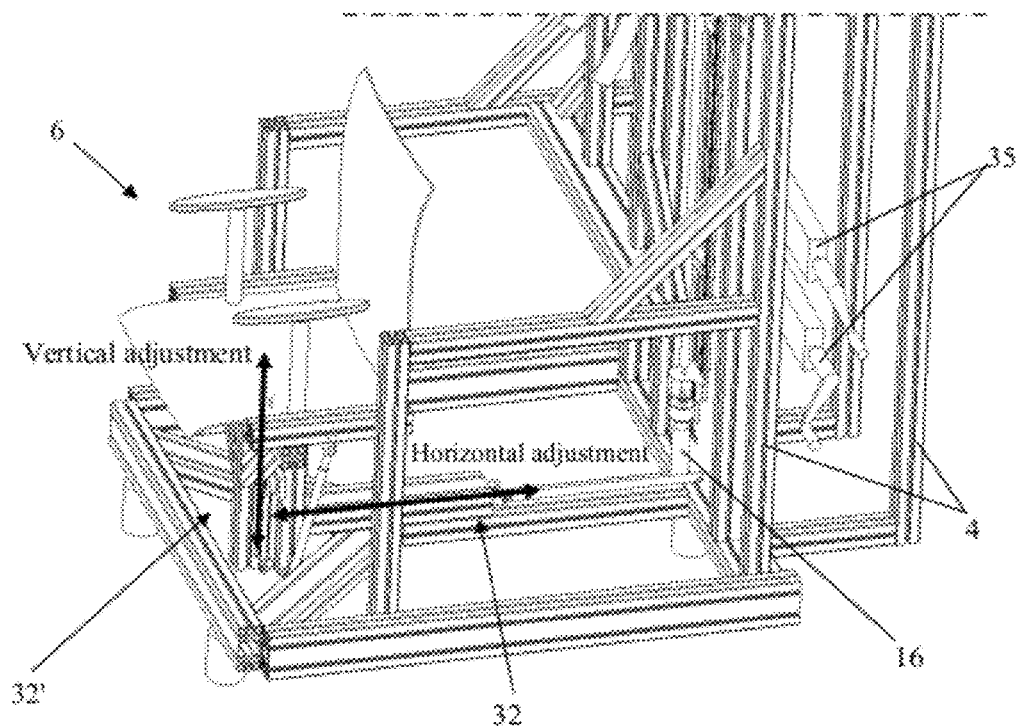
Figure 17:
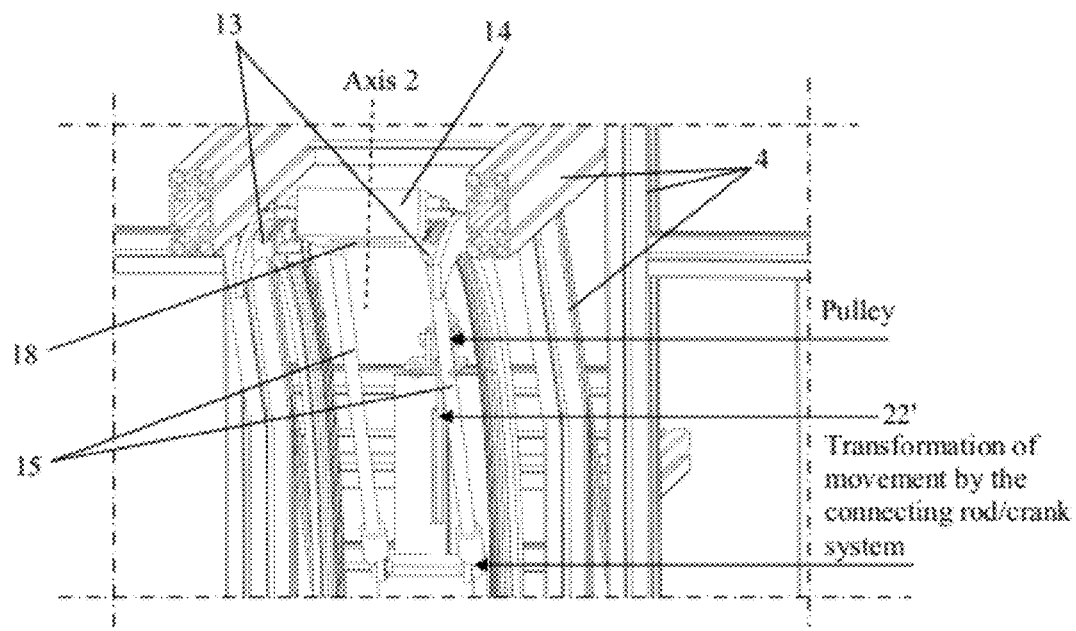
Figure 18:
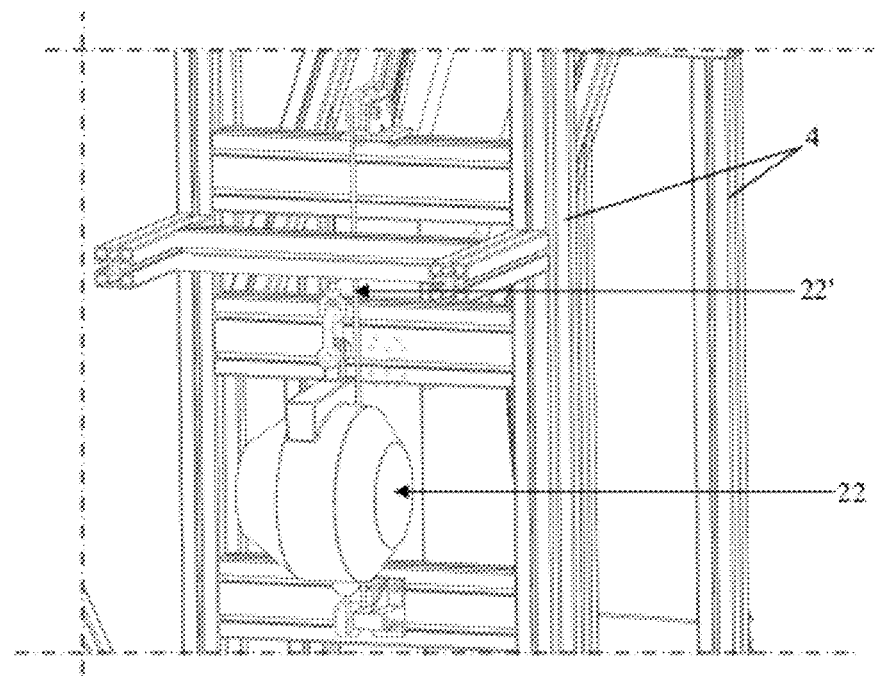
Figure 19:
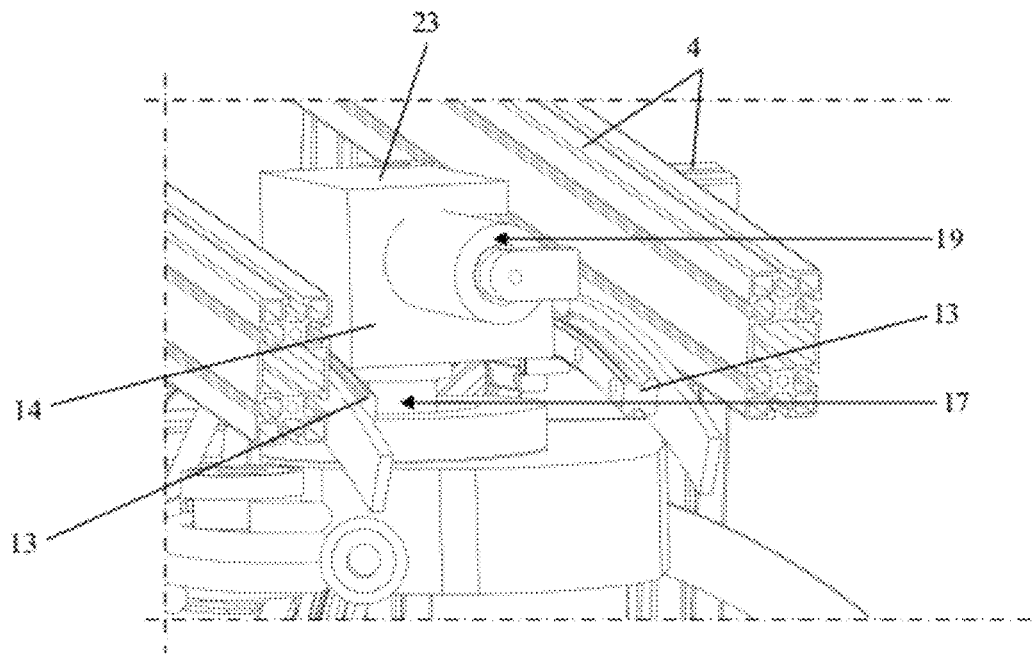
Figure 20:
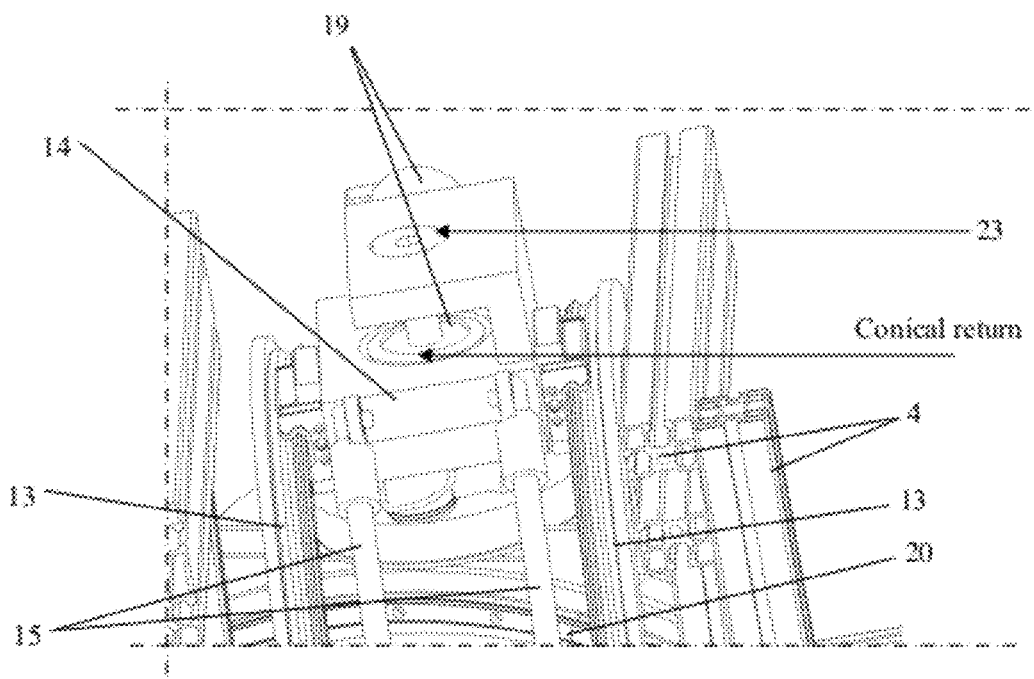
Figure 21A:
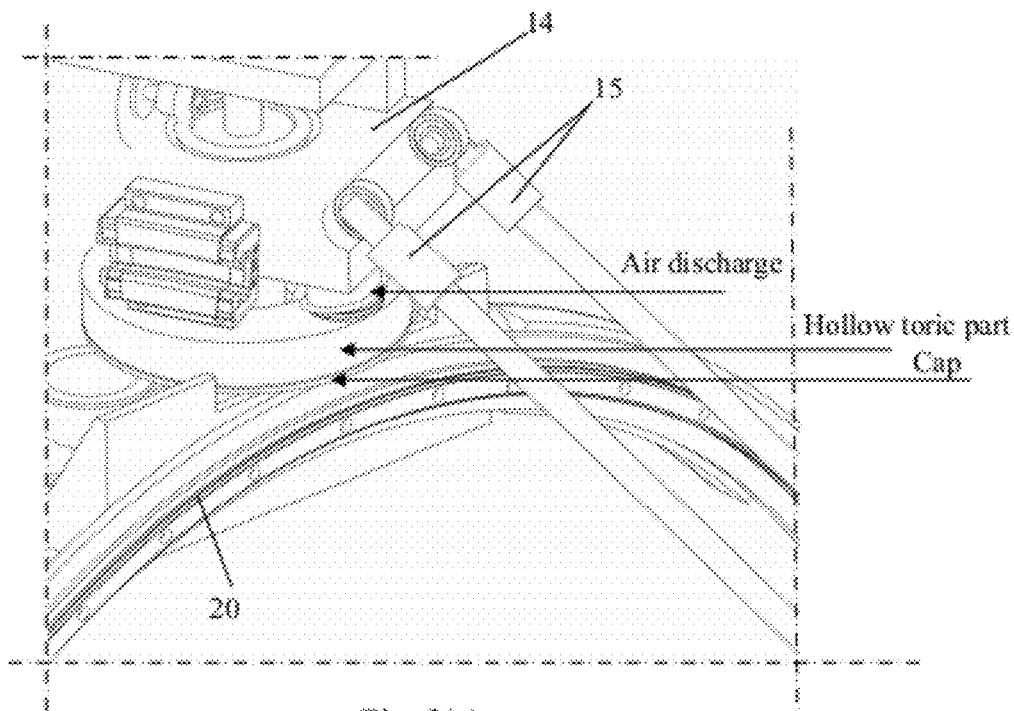
Figure 21B:
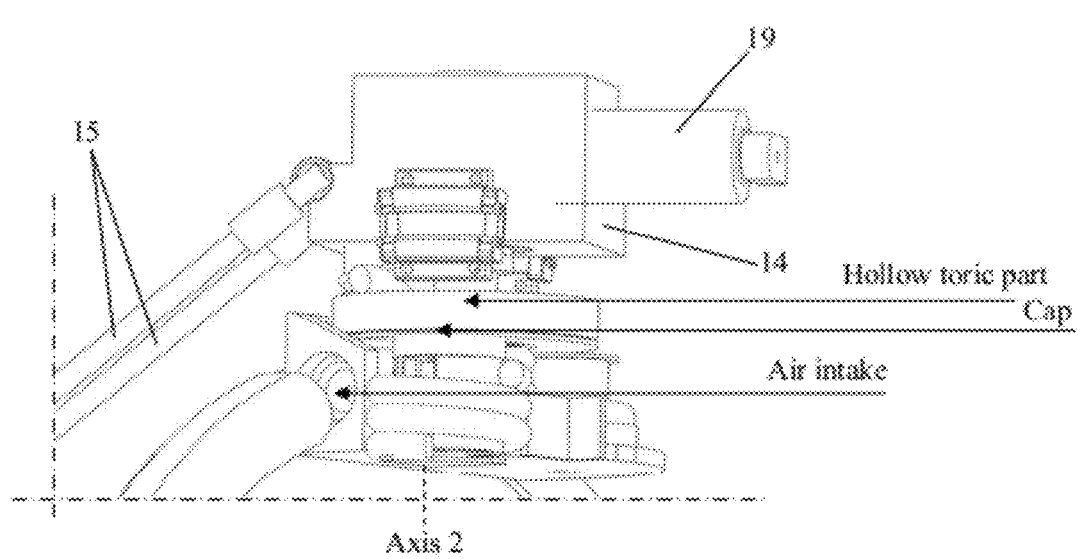
Figure 21C:
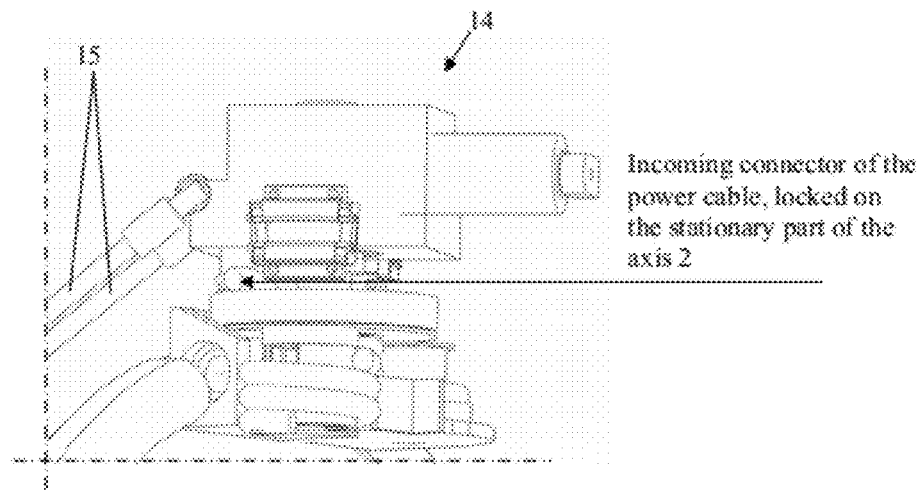
Figure 21D:
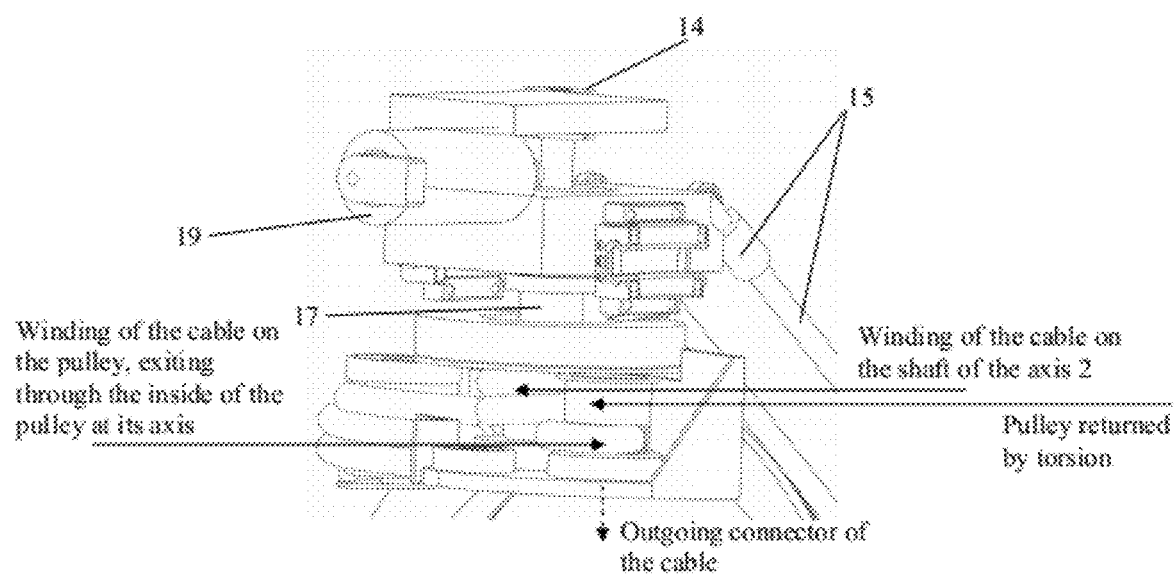
Figure 21E:
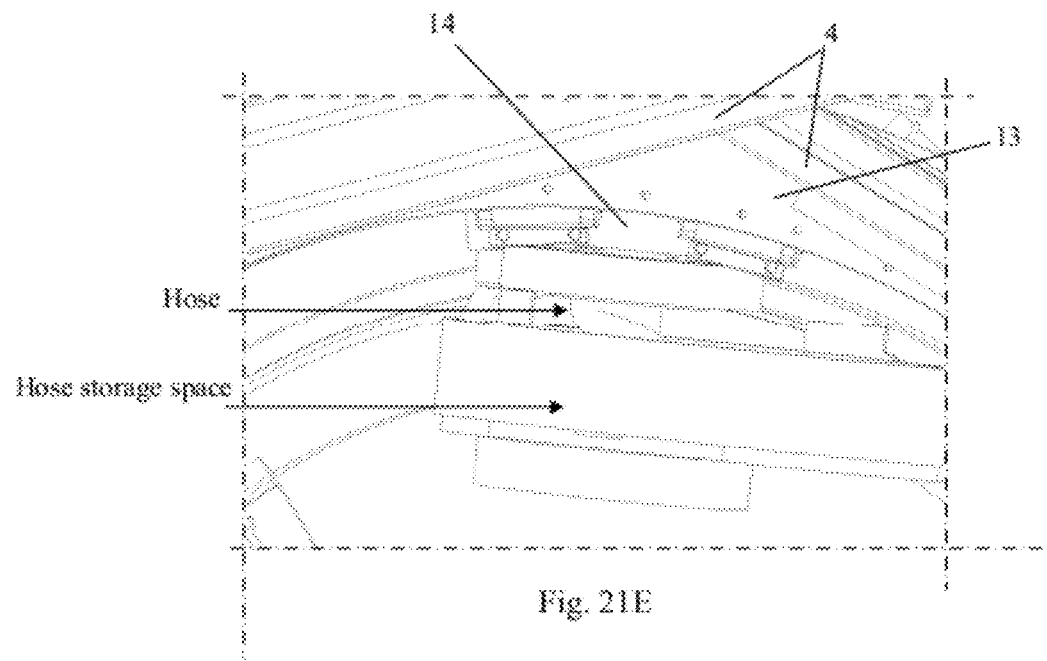
Figure 22:
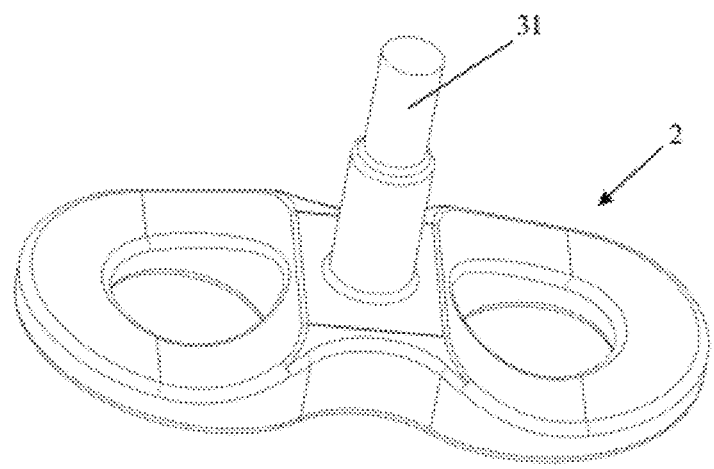

The invention will be better understood, using the description below, which relates to preferred embodiments, provided by way of non-limiting examples, and explained with reference to the accompanying diagrammatic drawings, in which:

FIGS. 1 to 4 are views that are respectively in perspective, in side elevation, in front elevation and from the top of a robotized installation according to the invention, used in relation to a transcranial magnetic stimulation probe, FIGS. 5A and 5B are perspective views, along two slightly different angles, of the robotized installation of FIGS. 1 to 4, the covering casing having been removed, FIG. 6A is an equivalent kinematic diagram of an embodiment, with four degrees of freedom, of the robotic device that is part of the robotized installation that is shown in FIGS. 1 to 5 or two sub-assemblies that constitute this device, FIG. 6B is an equivalent kinematic diagram of another embodiment with seven degrees of freedom of the robotic device that is part of the robotized installation shown in FIGS. 1 to 5, FIGS. 7A and 7B are perspective views of the robotized installation of FIGS. 1 to 5 that illustrate the end positions, respectively upper and lower end positions, of the first rotary articulation of the first sub-assembly of the robotic device and that show the movement at the level of this articulation, FIGS. 8A, 8B, 8C and 8D are views that are similar to those of FIGS. 7A and 7B illustrating four positions that are successively offset by 90° from the second rotary articulation of the first sub-assembly of the robotic device and that show the movement at the level of this articulation, FIGS. 9A and 9B are views that are similar to that of FIG. 8D illustrating the end positions (deployed and folded) of the third rotary articulation of the first sub-assembly of the robotic device and showing the movement at the level of this articulation, FIG. 10 is a gridded, relief view of a patient's head illustrating the accessible zone for the component or instrument carried by the robotic device without there being interference with the patient, FIGS. 11A and 11B are partial perspective views along two different angles, showing the second and third sub-assemblies of the robotic device that is part of the robotized installation of FIGS. 1 to 5 and illustrating the two end positions in translation of the second sub-assembly of the robotic device and showing its axis of movement, FIG. 12 is a partial side-elevation view of the object of FIGS. 11A and 11B illustrating the possible rotary movements at the first, second and third articulations that are part of the third sub-assembly of the robotic device, FIG. 13 is a partial perspective view of the third sub-assembly of the robotic device that is part of the robotized installation, whereby some of the constituent elements have a structure and an arrangement that are slightly different from the third sub-assembly shown in FIGS. 11A, 11B and 12, FIG. 14 is a partial top view of the robotized installation as shown in FIGS. 5A and 5B, partially showing certain elements of the articulations of the first sub-assembly of the robotic device, FIG. 15 is a partial side-elevation view of the robotized installation as shown in FIG. 5, showing more particularly the second and third rotary articulations of the first sub-assembly of the robotic device, as well as the sliding articulation forming the second sub-assembly of the robotic device, FIG. 16 is a partial detail and perspective view of the robotized installation as shown in FIG. 5, showing more particularly the seat that forms the device for supporting and holding the patient, as well as the devices for vertical and horizontal adjustments that are combined with it, FIGS. 17 and 18 are partial detail and perspective views of the robotized installation as shown in FIG. 5 that show more particularly the constituent elements of the safety device combined with the first rotary articulation of the first sub-assembly of the robotic device and produced in the form of a constant-tension return mechanism, FIGS. 19 and 20 are partial detail and perspective views of the robotized installation as shown in FIG. 5 showing more particularly the constituent elements of the first and second rotary articulations of the first sub-assembly of the robotic device, FIGS. 21A, 21B, 21C, 21D and 21E are partial detail and perspective views of the robotized installation as shown in FIG. 5, showing more particularly the elements of the air circulation circuit for cooling the probe, as well as the power cable of the probe, at the second rotary articulation of the first sub-assembly of the robotic device, and FIG. 22 is a perspective view of a transcranial magnetic stimulation probe that is part of a treatment device that comprises the robotized installation that is shown in FIGS. 1 to 5.

DETAILED DESCRIPTION OF THE INVENTION

The latter show a robotized installation 1 for the guided and controlled positioning and movement of a component or instrument 2 for diagnostic or surgical treatment, in particular an imagery probe or a transcranial magnetic stimulation probe or the like, at or around the head 3 of a patient 3'.

This installation 1 comprises essentially a support structure (frame) 4, covered by a covering and protection casing 4' and on which are mounted the constituent elements 7 to 31 of a robotic device 5 that forms a serial kinematic chain and that carries the above-mentioned component or instrument 2 at its free and position-controlled end. In addition, an adjustable device 6 for supporting and holding the patient 3', essentially in the seated position, is part of or is combined with said support structure 4.

According to the invention, said robotic device 5 consists of at least two 7, 7', preferably three 7, 7', 7", kinematic sub-assemblies that are mutually combined in series, comprising, on the one hand, a first sub-assembly 7 in the form of a rotary-articulation mechanism 8, 8', 8", integral with the support structure 4 by a first articulation 8 and corresponding to a series-type spherical kinematic arrangement with three degrees of freedom, whereby the articulation elements 8, 8', 8" are all located outside of the space 9 that can accommodate the patient 3' and their axes of rotation, axis 1, axis 2 and axis 3 being concurrent at a focal point PF corresponding essentially to the hypothetical center of the head 3 of the patient 3' in an intervention position, and, on the other hand, whereby a second sub-assembly 7' in the form of a mechanism with linear translation along an axis (axis 4) passes through the above-mentioned focal point PF and is integral with the moving part 10 of the third articulation 8" in series of the first sub-assembly 7, and, finally, if necessary, a third sub-assembly 7" in the form of a second rotary-articulation mechanism, integral with the moving part 12 of the second sub-assembly 7' and also corresponding to a series-type spherical kinematic arrangement with three degrees of freedom, whereby the articulation elements 11, 11', 11" of this third sub-assembly 7" exhibit concurrent axes of rotation: axis 5, axis 6, and axis 7.

The decomposition of the robotic device 5 into two, and even three, sub-assemblies 7, 7', 7" that are independent and connected to one another in a series facilitates control in position and in movement, increases the precision of the resulting movement and makes it possible to secure individually each of the articulation elements that constitute it.

In particular, the combination of a first sub-assembly 7 with spherical movement, formed by three rotary or rotoidal connections in series (8/axis 1, 8'/axis 2, 8"/axis 3) and not interfering with the space 9 accommodating the patient 3', with a second sub-assembly 7' with a movement in translation along a radial axis (axis 4) relative to the sphere or the spherical part whose points can be reached by means of the first sub-assembly 7, makes possible optimized management of the safety of the robotic device 5, optionally by the single secured control of this second sub-assembly 7'.

Consistent with the first characteristic of the invention, as is evident in particular from FIGS. 5, 14, 17, 19, and 20, the first rotary articulation 8 of the first sub-assembly 7 consists of a connection with a circular slide, comprising a guide rail 13, preferably a double rail, in the shape of an essentially semi-circular arc, integral with the support structure 4, and a moving carriage 14 that can circulate on said rail 13 and whose movement is controlled by a transmission linkage 15 that is connected to an actuator 16, whereby the circular movement is carried out in the median plane of the patient 3 in intervention position, and said guide rail 13 has a position and an extension such that it extends around the head 3 of said patient 3' essentially at the rear base of the skull up to the forehead.

The rail 13 is set rigidly at several locations at the support structure 4, at the level of an upper part in bracket form overhanging the device for supporting and holding the patient, in the form of an adjustable seat 6.

The rail 13 may have either a double structure (FIGS. 1 to 3, 7 to 9, 17, 19, and 20) or a structure with a single rail (FIGS. 5A, 5B and 14). In the first case, the carriage 14 circulates, at the level of suitable grooves, on the two identical rails that are parallel to one another via roller skids or portions of slides located on both sides of said carriage 14, and in the second above-mentioned case, the carriage 14 circulates on the single rail by means of at least two roller skids or with slides that are located one next to the other, on a single side.

The transmission linkage 15, ensuring the movement of the carriage 14 on the rail 13, can comprise, as is evident from FIGS. 5A and 5B, a pair of connecting rods connected to the carriage 14 by one end and to a second carriage that slides vertically in the support structure 14 by the other end. This second carriage can be driven in translation by the motor 16 by means of a ball screw and an endless lead screw engaging said second carriage at a wire nut (FIG. 5B).

The use of a first serial, spherical, articulated mechanism-type sub-assembly 7 with three degrees of freedom is particularly suited to a working volume of spherical shape, such as the space that surrounds a patient's head, whereby the positioning of the component 2 is carried out at the level of a sphere that is centered on the patient's head.

According to the invention, the sub-assembly 7 consists of a particular arrangement of circular guides (two concentric sub-assemblies with circular guiding connected to one another by an axis of rotation), thus avoiding any interference with the patient and optimizing the rigidity of the device to facilitate the precise handling of the component 2.

The safety mechanisms combined with the three rotary articulations 8, 8' and 8" ensure the safety of the patient in case of incident.

According to another characteristic of the invention and as FIGS. 14, 17, 19, 20, 21A and 21B show it, the second rotary articulation 8' of the first sub-assembly 7 consists of an axial articulation with a shaft 17 that is mounted to rotate in a bearing 18 that is provided in the moving carriage 14 that is part of the first rotary articulation 8, the movement in rotation of said shaft being controlled by an actuator 19, for example a geared motor unit, carried by said carriage 14.

According to another characteristic of the invention, as is evident in particular from FIGS. 5, 9, 15 and 19, the third rotary articulation 8" of the first sub-assembly 7 consists of a circular slide connection, preferably in the form of two rails 20, 21 that work in a sliding manner and that are each produced in the shape of an arc, whereby said rails 20 and 21 can be moved relative to one another between a folded arrangement in which they are essentially placed on top of one another, or that overlap over their entire length, and a deployed arrangement, in which they are no longer placed on top of one another except to a small extent.

As FIG. 15 shows by way of example of practical implementation, the stationary rail 20 can be equipped with a rolling segment 33 that extends over its entire length, and the rail 21 can be provided with several sets of ball bearings or needle bearings that are distributed over its length.

In addition, the stationary rail 20 can be equipped with an optical rule 34, and the moving rail 21 can be equipped with a corresponding optical sensor 34'.

The movement of the moving rail 21 relative to the stationary rail 20 can be carried out, for example, by means of a rack system or a drive-roller system, driven by means of a transmission that is adapted by an electric motor carried by the moving rail 21.

As the above-mentioned figures also show, the stationary rail 20 is assembled rigidly with the shaft 17 of the second rotary articulation 8', whereby the two rails 20 and 21 can be structurally locked in position relative to one another, by a mechanical connection or by locking the actuator, ensuring their mutual relative movement.

In the case of this third rotary articulation 8" locking, the first sub-assembly 7 constitutes a spherical articulated mechanism with two degrees of freedom, which can be adequate for certain applications that require a reduced mobility for the component or the instrument 2.

The locking of this articulation 8″ can be definitive or temporary, and in this latter case, it can be obtained consecutively to a corresponding software programming of the control unit of the electric motor that ensures the mobility of the rail 21 relative to the rail 20.

The shaft 17 that connects the rail 20 in a rotary manner to the carriage 14 preferably has a relatively small length, so as to reduce the cantilevers between the two connected elements and to ensure a good rigidity to the articulated assembly that is produced.

So as to avoid a possible drop of the robotic device 5 into the space 9 and to obtain an automatic release upward of said device, it may be advantageously provided that the moving carriage 14 of the first rotary articulation 8 be permanently forced in the upper end position by a return mechanism with constant tension 22, for example with a cable 22′ (FIGS. 5, 17 and 18).

In addition, for the purpose of avoiding any uncontrolled movement of the elements attached to the shaft 17, optionally able to interfere with the patient 3′, a device 23 for locking the shaft 17 in rotation is combined with the actuator 19, for example in the form of an active brake in the event of power failure at the latter, for example of the electromagnetic type, whereby said device 23 can be unlocked by an operator by means of a manual command for current supply, so as to authorize a free rotation of the shaft 17 around its axis of rotation, axis 2 (FIGS. 20 and 21D).

By way of additional safety at the level of the first sub-assembly 7, it can also be provided that the actuator 21′ of the third rotary articulation 8″ of the first sub-assembly 7 produces a locking in mutual position of the two rails 20 and 21 in the event of a power failure.

According to a characteristic of the invention that is evident in particular from FIGS. 11 and 15, making it possible to control the application pressure of the component or instrument 2 against the head 3 of the patient 3′, a force sensor is combined with the second sub-assembly 7′, making it possible to produce a force control of said second sub-assembly 7′ in the translation direction (axis 4) that is essentially perpendicular to the surface of the head 3 of the patient 3′ in intervention position, whereby this sub-assembly 7′ also comprises a return mechanism, for example of the mechanical type, forcing the component or instrument 2 remotely from the surface of the head 3 of the patient 3′.

The force sensor can either be mounted in the sub-assembly 7′ or be integrated directly in the component or instrument 2.

In particular, in the case of a probe-type component 2 for transcranial magnetic stimulation or the like (component 2 designed to be applied against a patient's head), said force sensor can be integrated into the component or the instrument 2 that is carried by the robotic device 5, whereby said force sensor is part of a force control of the second sub-assembly 7′ of said device 5.

The force sensor can then come in the form of a thin sensor in the form of a sheet portion such as, for example, the sensors known under the designation FLEXIFORCE (filed name) of the Tekscan Company or under the designation FSR (filed name) of the Interlink Electronics Company. This sensor will be insensitive to the radiation that is optionally emitted by the component 2.

FIG. 15 shows (partially in cutaway) the motor/coder unit 35 that ensures the controlled actuation of the slide connection that forms the second sub-assembly 7′, as well as the return spring that forms the safety mechanism of this connection.

According to a first variant embodiment of the invention, shown in a diagrammatic and kinematic manner in FIG. 6, the robotized installation 1 comprises a robotic device 5 with four degrees of freedom, integrating the first and second sub-assemblies 7 and 7′, whereby such a device makes it possible to reach with the component or instrument 2 all of the points that are shown in FIG. 10.

Consistent with a second variant embodiment of the invention and as is evident from FIGS. 1 to 5 and 7 to 13 and shown diagrammatically and kinematically in FIG. 6B, the robotized installation 1 comprises a redundant robotic device 5 with seven degrees of freedom, integrating the first, second, and third sub-assemblies 7, 7′ and 7″, whereby the third sub-assembly 7″ consists of a mechanism with three rotary articulations in a series 11, 11′, 11″ forming a spherical wrist.

Such a robotic device, consistent with the second variant, exhibits not only the same properties as the first above-mentioned variant (that it integrates), but it also makes it possible to produce a local orientation of the component or instrument 2 relative to a given reference point PR, for example, the point of contact or central point of the contact surface between the component 2 and the head 3 of the patient 3′ (optionally combined with the central point of the component 2).

This additional property of the second variant is necessary in particular within the scope of the transcranial magnetic stimulation to ensure the condition that the probe 2 and the head 3 be tangent during the treatment procedure requiring a controlled scanning movement of said probe.

Consistent with a practical implementation of the invention, shown more particularly in FIGS. 11 to 13 of the accompanying drawings, the third sub-assembly 7″ that forms the spherical wrist essentially consists of a first articulation 11 that is formed by a rail 24 in an arc that is integral with the moving part 12 of the second sub-assembly 7′ and on which circulates a carriage 25 whose movement is controlled by an actuator 26, by a second articulation 11′ that is formed by two arms 27 that are mounted rigidly on the moving carriage 25 by one of their ends and each carrying at their opposite ends a stationary carriage 28 that each works (curvilinear slide) with a moving rail portion 29 in the shape of an arc, and parallel between then, and by a third articulation 11″ in the form of a bearing plate 30, integral with moving rails 29 and able to accommodate with ease of rotation (around axis 7) a hub 31 that is integral with the component or instrument 2.

The actuator 36 (for example an electric motor) that ensures the movement of the moving rails 29 in the carriages 28 can, for example, be carried by the arms 27, whereby the transmission of the movement is ensured through or around the latter (capstans).

Likewise, the actuator 37 (electric motor) that ensures the rotation of the component 2 around its hub 31 (axis 7) can be carried directly by the bearing plate 30 that accommodates the component 2.

The maximum angular ranges for the articulations 11, 11′ and 11″ that form the third sub-assembly 7″, as well as for the articulations 8, 8′ and 8″, are determined during the design of the robotic device 5 by evaluating (on the basis of a three-dimensional reconstruction of the patient's head from MRI images, for example) the necessary angles to ensure that the front face of the probe 2 is tangent to the various regions of the head that are to be reached.

In addition, possible offsets between the center of the patient's head and the focal point PF are also to be taken into consideration in the production of the sub-assembly 7″.

An additional description of the invention, in direct relation to the accompanying drawings, is presented below, more specifically but not in a limiting way, within the scope of an application to the transcranial magnetic stimulation.

As FIGS. 1 to 5 and 7 to 9 show, the robotized installation 1 essentially comprises a rigid support structure 4 (for example, in the form of an assembly of non-magnetic, metallic segments), a crankcase (casing or covering 4'), an adjustable seat 6, and a robotic device 5 that has seven degrees of freedom. The robotic device 5 allows the positioning of a component or instrument 2 by movement around a fixed point PF in space. It also makes possible the positioning of a probe 2 for imagery or stimulation around the head 3 of a patient 3'. Any other device that should be kept in contact in a reliable way with the head can also be considered.

In the case of the above-mentioned figures, the robotic device 5 is shown with an effector (probe 2) that makes possible the implementation of a transcranial magnetic stimulation (SMT) treatment.

As is evident from FIGS. 1 to 9, 10 to 15 and 17 to 20, the robotic device 5 consists of three sub-assemblies 7, 7' and 7" that are mounted in series: a primary structure 7 with three degrees of freedom, a sliding connection 7' that is actuated, and a spherical wrist 7" with three degrees of freedom.

The primary structure 7 allows the placement and movement of the center of the transcranial magnetic stimulation probe 2 on a sphere that is centered on the patient 3'. On a kinematic level, it involves a spherical-series robot structure (FIG. 6).

The use of circular guides for the production of the first and third rotary articulations 8 and 8" makes it possible to obtain movements without interference with the patient 3' by ensuring the necessary rigidity of the device 5.

The maximum movements that can be obtained at each of the articulations 8, 8' and 8" are indicated in FIGS. 7 to 9. These movements make it possible to reach the gridded surface that is shown in FIG. 10: this surface corresponds to the entire cranial cap, delimited by the brain (front and upper parts of the skull, forehead, temples, ears). The arrangement of the connections (articulations 8, 8' and 8") and the possible amplitude of movements at these rotary or rotoidal connections make it possible to ensure a movement over this zone with a precision that is compatible with the SMT treatment, by obtaining in particular an isotropy index for the structure that is more than 0.8.

As FIGS. 6, 11, 12 and 15 show, the actuated slide connection (second sub-assembly 7') makes possible the movement of the probe 2 in contact with the patient 3'. The actuation direction (axis 4), close to the perpendicular line at the surface of the patient's head 3, makes it possible to manage the probe/patient contact force in a simple manner: force control is achieved by controlling this single axis (axis 4). The sliding connection 7' is returned to position by a mechanical device (for example, of the prestressed spring type). If the power fails, the probe 2 tends to remove the patient, ensuring the safety of the latter.

The spherical wrist (sub-assembly 7"/FIGS. 11, 12 and 13) makes it possible to impose the condition that the plane of the probe 2 be tangent to the patient's head 3, required by the treatment. The actual rotation of the probe (axis 7) makes it possible to orient the magnetic field and to excite the cortical furrows as well as possible.

The behavior of the robotic device 5 is reliable in the case of voluntary or involuntary power failure (emergency stopping, end of use, current failure): the rotary articulation 8 around the axis 1 for movement in rotation then returns to the upper vertical position (FIG. 7A) by a constant-tension return system (FIGS. 17 and 18), preventing the device from being dropped on the patient.

Likewise, the return device that is combined with the sliding connection will automatically separate the probe from the patient's head 3 in the case of a similar incident.

As FIGS. 14, 15, 19 and 20 show more particularly, the articulation 8' that provides a movement in rotation around the axis of the shaft 17 (axis 2) is guided using an electric motor that engages on a perpendicular axis (shaft 17). This axis makes it possible to obtain the desired rotation by means of a reducing agent, for example, a conical pinion that engages with a gear that is integral with the shaft 17. The latter is also connected to a braking device 23 via power failure. If power is eliminated, the braking and the locking of the rotation are ensured, preventing any uncontrolled movement around the articulation 8' and optional interferences with the patient.

Exiting from the space 9 is, however, to be possible even in the case of failure of the robotized installation 1. If at this time the probe 2 is located, for example, facing the patient 3', hampering him in his exiting movement, an operator can manually intervene to send a current selectively into the brake 23 and to manually orient the robotic device 5 (in one of the positions of FIGS. 8A and 8D).

FIG. 22 shows an SMT probe of standard form with the general composition and comprising a rear means 31 that allows its mounting in rotation in the bearing plate 30 of the spherical wrist that forms the third sub-assembly 7".

As an active element, the probe comprises a rolling of copper in the shape of an 8, making possible the creation of an intense magnetic field. The good operation of the probe 2 requires its cooling, for example by circulation of air.

Actually, the creation of the magnetic field at the SMT probe 2 causes the heating of the copper conductor that composes it. To ensure correct operation, cooling is therefore to be ensured.

Furthermore, the movements of the patient 3' are detected using an external locater, making it possible to determine the position and the orientation of the patient's head. So as to ensure the good operation of this locater, it is necessary to minimize the presence of cables and hoses around the robotic device 5. The presence of cables could also disturb the patient or the operator during the use of the device.

Consequently, the robotic device 5 is designed so as to integrate a hose that makes it possible to cool the SMT probe 2 by taking in air from an aspirator or an analogous vacuum device that is integrated with the installation 1, as well as the power cable that makes it possible for the probe to operate.

Examples of solutions to manage the path of the hoses at the second and third articulations 8' and 8" (axis 2 and axis 3) are shown in the FIGS. 21A to 21F. In the two cases, the power functions in current and air circulation are decoupled.

At the articulation 8' (axis 2), an O-ring-like rotary joint is created around the pivoting connection that constitutes the articulation 8' (axis 2/FIGS. 21A and 21B). This joint consists of a hollow toric part and a cap that is flattened against the latter to ensure air tightness. The air circulates in the cavity of the toric part to pass between the two units in a relative movement at the level of the articulation 8'.

For this articulation 8', the power cable does not pass through the axis of rotation of the connection.

So as to manage the variation in length of the cable that results therefrom, a winding system is installed. This system consists of a cylindrical surface that is located on the rotation shaft 17 that provides the axis 2 (FIGS. 21C and 21D), around which the hose is wound, and a pulley that is called back in rotation on which the cable then advances. The cable penetrates inside this pulley to exit therefrom at its axis of rotation. As soon as a rotation around the articulation causes an extension of the side of the cable, the excess is wound up on the pulley automatically.

At the articulation 8" (axis 3), the variation of length of arc (FIG. 9) is managed, for taking in air, by the use of a compressible hose. The variation in length is therefore absorbed by reducing the apparent length of the hose. The variation of length of the power cable is taken into account by the installation of a pulley with return by torsion spring.

The implementation of the robotized installation 1 according to the invention, in the SMT application or an analogous application, assumes an initial positioning of the patient 3' so as to offset the center PF of the spherical primary mechanism (first sub-assembly 7) with the center of the head 3. The seat 6 is therefore equipped with two adjustment devices 32 and 32', in the horizontal and vertical directions, each combined with a respective manual control component 32" (for example, a crank). The positioning procedure will comprise a manual adjustment facilitated by this continuous adjustment device along two degrees of freedom and will be based either on the estimation of the position of the head from an external locater or by an optical indication of the center PF of the spherical mechanism (sub-assembly 7) projected onto the patient 3'.

Two surgical strategies can be considered after an initial adjustment of the patient's head into the space 9 relative to the focal point PF of the first and second sub-assemblies 7 and 7' (projection of a cross on the forehead of the patient).

According to a first possibility, the patient—and in particular the patient's head—is held in position after adjustment so as to prevent an offsetting between the predetermined path of the probe 2 and the zones to be treated.

According to a second possibility, allowing a certain freedom of movement of the patient, the patient is equipped with passive markers (for example, a headband with markers surrounding his head or a mask placed on his face) that can be detected by corresponding position sensors (for example, two infrared or optical cameras at 90°). The data from these sensors are provided continuously to the control and guiding unit of the robotized installation 1, which will modify the precalculated path of the probe 2 based on possible movements of the patient, in the manner of real-time movement control. Such a locating system is tracked and is, for example, known by the NDI, Inc., Company under the designation POLARIS.

The various actuators of the rotary articulations of three sub-assemblies 7, 7' and 7" preferably consist of electric motors (for example, with direct current or with harmonic excitation) combined with mechanisms for transmission and/or reduction of movements and with sensors of positions and/or coders, well known in the field of robotics, whereby all of these actuators are guided by a suitable control and guiding unit, for example, a computer unit, also calculating and storing the path of the component 2 from data that are programmed or deduced from preceding images.

The robotized installation 1 according to the invention thus makes it possible to satisfy the above-cited requirements for precision (positioning at nearly 1 mm) and safety (active and passive), and to meet constraints associated with an automated procedure in the medical environment.

This invention also has as its object a device for treatment by transcranial magnetic stimulation, essentially comprising a probe 2 that comprises a magnetic stimulation coil and carried by a robotized installation 1.

This device is characterized in that the robotized installation 1 consists of an installation as described above and illustrated by way of example in the accompanying figures and integrates a robotic device 5 with seven degrees of freedom, which can produce automatic positioning and movement of said probe around the head of a patient based on a previously determined path, under the monitoring of a control and guiding unit.

Providing a robotic device 5 with seven degrees of freedom, i.e., a redundant degree of freedom, makes possible a satisfactory kinematic behavior and the guarantee of a movement and a precise positioning at the level of each articulation, as well as control-optimized safety.

Preferably, this device also comprises a locating system, preferably in position and in orientation, of the head 3 of the patient 3' in the space 9 that accommodates the patient, working with the control and guiding unit for the purpose of carrying out an adjustment of the head 3 relative to the focal point PF of the first sub-assembly 7 of the robotic device 5 and a control, based on movements of the head 3, from the position of the probe 2 by means of the robotized installation 1, under the monitoring of the control and guiding unit and based on signals or data provided by the locating system.

Such a device makes it possible to replace the operator during an SMT procedure by ensuring the required precision and safety.

The primary characteristics of a transcranial magnetic stimulation device of the above-mentioned type are evident in particular from the document "Robotic Image-Guided Transcranial Magnetic Stimulation," Lebosse, C. et al., Computer-Assisted Radiology and Surgery, Volume 1, Osaka, Japan 2006, whose entire contents are integrated into the present by reference.

Finally, the invention also relates to a process for transcranial magnetic stimulation that uses the device described above.

This process essentially consists in successively carrying out the following stages:

Production of several images of the brain and the head of the patient to be treated, for example by MRI or fMRI;

Manufacture of a three-dimensional model of the brain and the head of the patient;

Determination of the cortical regions to be stimulated and their respective order in the stimulation sequence, as well as the frequency, of the duration and, if necessary, the power of stimulation for each region;

Calculation by the control and guiding unit of the device, or by a unit for external calculation of the path of the functional center of the coil of the probe around the head of the patient to stimulate optimally each cortical region in question based on the predetermined specificities;

Positioning of the patient in the robotized installation and implementation of adjustment or framing of his head relative to the focal point of the robotized installation and to the three-dimensional model;

Start-up and autonomous execution of the stimulation procedure with controlled movement of the probe by the robotic device, with optional acquisition of the location and the orientation of the probe for analysis subsequent to treatment.

More specifically, after the identification of cortical regions to be stimulated, the path from the center of the coil of the probe 2 is calculated, as well as the orientation of said probe throughout the path, for an optimum stimulation of said regions, on the basis of a three-dimensional reconstitution of the head of the patient.

The movement speed of the probe, as well as the power, the frequency, and the number of sequences for stimulation per region to be stimulated are calculated or programmed.

The calculation of the required path, which also takes into account the physical and mechanical constraints of the robotic device (angular limits of rotation of the articulation, limits in terms of speed of rotation of the articulations, avoiding collision), can, for example, be produced at the control and guiding unit by means of a probabilistic-movement planning algorithm, for example based on an algorithm that uses samples and is derived from "Probabilistic Road Maps for Path Planning in High Dimensional Configuration Spaces," Kavraki, L. et al., IEE Transaction on Robotics and Automation, 1996, Volume 12, pages 566 to 580.

Furthermore, a pseudo-inverse velocity monitoring technique is used to carry out the movement of the probe 2 (see, for example: Advanced Robotics: Redundancy and Optimization," Nakamura, Y., Addison-Wesley Longman Publishing, Boston, 1991).

Of course, the invention is not limited to the embodiments that are described and shown in the accompanying drawings. Modifications remain possible, in particular from the standpoint of the composition of the various elements or by substitution of equivalent techniques, without thereby going outside the field of protection of the invention.

The invention claimed is:

1. A robotized installation configured for guided and controlled positioning and movement of a transcranial magnetic stimulation probe at or around a head of a patient, comprising:
   a support structure on which are mounted constituent elements of a robotic device forming a serial kinematic chain and carrying the probe at a free and position-controlled end; and
   an adjustable device for supporting and holding the patient, in a seated position, forming part of or being combined with said support structure, wherein
   said robotic device (5) comprises three (7, 7', 7") kinematic sub-assemblies that are mutually combined in series and that comprise:
   i) a first sub-assembly (7) comprising a rotary-articulation mechanism having first, second and third articulation elements (8, 8', 8"), integral with the support structure (4) by the first articulation element (8) and corresponding to a serial spherical kinematic arrangement with three degrees of freedom, and the first, second and third articulation elements (8, 8', 8") are all located outside of a space (9) that can accommodate the patient (3') and comprise respective axes of rotation, axis 1, axis 2, and axis 3, whereby axes of rotation, axis 1, axis 2, and axis 3 are concurrent at a focal point (PF) that corresponds approximately to a hypothetical center of the head (3) of the patient (3') in an intervention position,
   ii) a second sub-assembly (7') comprising a mechanism with linear translation along an axis 4 that passes through the focal point (PF) and is integral with a moving part (10) of the third articulation element (8") in series of the first sub-assembly (7), and,
   iii) a third sub-assembly (7") comprising a second rotary-articulation mechanism, integral with a moving part (12) of the second sub-assembly (7') and making possible imposition of tangency of a plane of the probe (2) relative to the head (3) of the patient, wherein said third sub-assembly (7") is a serial spherical kinematic arrangement forming a spherical wrist and comprising three separate rotary articulation elements (11, 11' and 11") arranged in series and whose respective axes of rotation, axis 5, axis 6 and axis 7, are mutually concurrent at a point (PR) adapted to correspond to a point of contact between the probe (2) and the head (3) of the patient (3').

2. The installation according to claim 1, wherein the first rotary articulation (8) of the first sub-assembly (7) comprises a circular sliding connection, comprising a guide rail (13), comprising an essentially semi-circular arc, integral with the support structure (4), and a moving carriage (14) that can circulate on said guide rail (13) and whose movement is controlled by a transmission linkage (15) that is connected to an actuator (16), whereby a circular movement is carried out in a median plane of the patient (3) in the intervention position, and said guide rail (13) has a positioning and an extension adapted to extend around the head (3) of said patient (3') essentially at a rear base of a skull up to a forehead.

3. The installation according to claim 2, wherein the second rotary articulation element (8') of the first sub-assembly (7) comprises an axial articulation with a shaft (17) that is mounted to rotate in a bearing (18) that is provided in the moving carriage (14) that is part of the first rotary articulation element (8), whereby movement in rotation of said shaft is controlled by an actuator (19) or a geared motor unit, carried by said carriage (14).

4. The installation according to claim 3, wherein one (20) of the rails (20, 21) forms the third rotary articulation element (8") and is assembled rigidly with the shaft (17) of the second rotary articulation element (8') of the two rails (20 and 21), and the two rails can be structurally locked in position relative to one another, by mechanical connection or by locking of the actuator or geared motor unit, ensuring mutual relative movement of the two rails.

5. The installation according to claim 3, wherein a device (23) for locking the shaft (17) in rotation is combined with the actuator (19) or geared motor unit, to form an active brake in an event of a power failure at the level of the actuator or geared motor unit, whereby said device (23) can be unlocked by an operator by means of a manual control for current supply, so as to allow a free rotation of the shaft (17) around the shaft's axis of rotation which is axis 2.

6. The installation according to claim 3, wherein the actuator or geared motor unit is an electromagnetic actuator or geared motor unit.

7. The installation according to claim 2, wherein the moving carriage (14) of the first rotary articulation element (8) is permanently stressed in an upper end position by a constant-tension return mechanism (22) or a cable (22').

8. The installation according to claim 2, wherein the rail is a double rail.

9. The installation according to claim 1, wherein the third rotary articulation element (8") of the first sub-assembly (7) comprises a circular slide connection comprising two rails (20, 21) that work in a sliding manner and that are each in a shape of an arc, whereby said rails (20 and 21) can be moved relative to one another between a folded arrangement in which the two rails are essentially placed on top of one another, or overlap over an entire length of the two rails, and a deployed arrangement, in which the two rails are no longer placed on top of one another except on a small part.

10. The installation according to claim 9, wherein an actuator of the third rotary articulation element (8") of the first sub-assembly (7) carries out a locking in mutual position of the two rails (20 and 21) in an event of a power failure.

11. The installation according to claim 1, wherein a force sensor is combined with the second sub-assembly (7'), to produce a force control of said second sub-assembly (7') in the translation direction along axis 4 that is essentially perpendicular to a surface of the head (3) of the patient (3') in the intervention position, whereby the second sub-assembly (7') also comprises a return mechanism, forcing the probe remotely from the surface of the head (3) of the patient (3').

12. The installation according to claim 11, wherein the return mechanism is a mechanical return mechanism.

13. The installation according to claim 1, wherein the installation further comprises a redundant robotic device (5) with seven degrees of freedom, integrating the first, second and third sub-assemblies (7, 7' and 7"), whereby the third sub-assembly (7") comprises a mechanism with three rotary articulations in a series (11, 11', 11") forming a spherical wrist with three degrees of freedom.

14. The installation according to claim 13, wherein the third sub-assembly (7") that forms the spherical wrist comprises a first articulation (11) that is formed by a rail (24) in an arc that is integral with the moving part (12) of the second sub-assembly (7') and on which circulates a carriage (25) whose movement is controlled by an actuator (26), by a second articulation (11') that is formed by two arms (27) that are mounted rigidly on the moving carriage (25) by one of their ends and the two arms carrying at their opposite ends a stationary carriage (28), and each stationary carriage works with a corresponding moving rail portion (29) in a shape of an arc, and parallel between the moving rail portions, and by a third articulation (11") comprising a bearing plate (30), integral with the moving rails (29) and able to accommodate with axis of rotation 7 a hub (31) that is integral with the component probe.

15. The installation according to claim 1, wherein a force sensor is integrated in the probe that is carried by a robotic device (5), whereby said force sensor is part of a force control of the second sub-assembly (7').

16. The installation according to claim 15, wherein the force sensor is a pressure sensor.

17. A device for treatment by transcranial magnetic stimulation, comprising a probe that comprises a magnetic stimulation coil and is carried by a robotized installation, the device comprising the installation according to claim 1, integrating a robotic device (5) with seven degrees of freedom, which is able to produce automatic positioning and movement of said probe (2) around the head (3) of the patient (3') based on a previously determined path, under monitoring of a control and guiding unit.

18. The device according to claim 17, further comprising a locating system of the head (3) of the patient (3') in the space (9) that accommodates the patient, working with the control and guiding unit for the purpose of carrying out an adjustment of the head (3) relative to the focal point (PF) of the first sub-assembly (7) of the robotic device (5) and a control, based on movements of the head (3), of the position of the probe (2) by means of the robotized installation (1), under the monitoring of the control and guiding unit and based on signals or data provided by the locating system.

19. A process for transcranial magnetic stimulation that uses the robotized installation according to claim 1, comprising:

producing several images of the brain and the head of the patient to be treated;

manufacturing a three-dimensional model of a brain and of the head of the patient;

determining cortical regions to be stimulated and their respective order in the stimulation sequence, as well as frequency, duration and, a power of stimulation for each region;

calculating by the control and guiding unit of the device, or by a unit for external calculation of the path of the functional center of the coil of the probe around the head of the patient to stimulate optimally each cortical region in question based on predetermined specificities;

positioning of the patient in the robotized installation and implementation of adjustment or framing of the head relative to the focal point of the robotized installation and to the three-dimensional model; and start-up and autonomous execution of the stimulation procedure with controlled movement of the probe by the robotized installation, optionally with acquisition of the location and the orientation of the probe for analysis subsequent to treatment.

20. A robotic device for controlling and manipulating a transcranial magnetic stimulation probe, comprising:

i) a first sub-assembly comprising a rotary-articulation mechanism having first, second and third articulation elements, and corresponding to a serial, spherical kinematic arrangement with three degrees of freedom, and the first, second and third articulation elements are all located outside of a space that can accommodate a patient and comprise respective axes of rotation, axis 1, axis 2, and axis 3, which are concurrent at a focal point PF that corresponds approximately to a hypothetical center of a head of a patient in an intervention position;

ii) a second sub-assembly comprising a mechanism with linear translation along an axis 4 that passes through the focal point PF and is integral with a moving part of the third articulation element in series of the first sub-assembly; and iii) a third sub-assembly comprising a second rotary-articulation mechanism, integral with a moving part of the second sub-assembly and making possible to impose tangency of a plane of the probe relative to the head of the patient, wherein said third sub-assembly is a serial spherical kinematic arrangement forming a spherical wrist and comprising three separate rotary articulation elements arranged in series and whose respective axes of rotation, axis 5, axis 6 and axis 7, are mutually concurrent at a point PR adapted to correspond to a point of contact between the probe and the head of the patient.

* * * * *